United States Patent
Kim et al.

(10) Patent No.: US 9,327,049 B2
(45) Date of Patent: May 3, 2016

(54) ANTI-ADHESION POLYMER COMPOSITION CAPABLE OF SUPPORTING GROWTH FACTOR

(75) Inventors: Jung Ju Kim, Gyeonggi-Do (KR); Jung Won So, Gyeonggi-Do (KR); Hyun Seung Ryu, Gyeonggi-Do (KR); Jun Hyuk Seo, Gyeonggi-Do (KR)

(73) Assignee: CG Bio Co., Ltd., Gyeonggi-Do (KR)

( * ) Notice: Subject to any disclaimer, the term of this patent is extended or adjusted under 35 U.S.C. 154(b) by 0 days.

(21) Appl. No.: 14/374,988

(22) PCT Filed: Mar. 8, 2012

(86) PCT No.: PCT/KR2012/001689
§ 371 (c)(1),
(2), (4) Date: Jul. 28, 2014

(87) PCT Pub. No.: WO2013/129719
PCT Pub. Date: Sep. 6, 2013

(65) Prior Publication Data
US 2015/0010490 A1    Jan. 8, 2015

(30) Foreign Application Priority Data
Feb. 28, 2012  (KR) ........................ 10-2012-0020554

(51) Int. Cl.
| | | |
|---|---|---|
| *A61K 31/74* | (2006.01) | |
| *A61L 24/04* | (2006.01) | |
| *A61L 31/16* | (2006.01) | |
| *A61L 31/04* | (2006.01) | |
| *A61L 24/00* | (2006.01) | |
| *C08L 71/02* | (2006.01) | |
| *A61K 47/30* | (2006.01) | |
| *A61K 47/10* | (2006.01) | |
| *A61K 47/34* | (2006.01) | |

(52) U.S. Cl.
CPC ............ *A61L 24/046* (2013.01); *A61L 24/0015* (2013.01); *A61L 24/043* (2013.01); *A61L 31/041* (2013.01); *A61L 31/16* (2013.01); *C08L 71/02* (2013.01); *A61B 2090/0816* (2016.02); *A61K 47/10* (2013.01); *A61K 47/30* (2013.01); *A61K 47/34* (2013.01); *A61L 2300/252* (2013.01); *A61L 2300/414* (2013.01); *A61L 2400/04* (2013.01); *A61L 2400/06* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 4,188,373 A | 2/1980 | Krezanoski | |
| 4,474,751 A | 10/1984 | Haslam et al. | |
| 4,478,822 A | 10/1984 | Haslam et al. | |
| 5,036,046 A * | 7/1991 | Neufeld | A61K 31/00 514/20.8 |
| 6,280,745 B1 | 8/2001 | Flore et al. | |
| 6,294,202 B1 | 9/2001 | Burns et al. | |
| 2008/0213188 A1* | 9/2008 | Ferrari | A61K 49/0043 424/9.6 |
| 2010/0130550 A1* | 5/2010 | Aberg | A61K 9/0048 514/324 |
| 2011/0229432 A1 | 9/2011 | Choi et al. | |
| 2012/0156164 A1 | 6/2012 | Park et al. | |

FOREIGN PATENT DOCUMENTS

| | | |
|---|---|---|
| KR | 1020100090409 A | 8/2010 |
| KR | 1020110074006 A | 6/2011 |
| WO | 2005/044285 A1 | 5/2005 |
| WO | 2008/132233 A1 | 11/2008 |

\* cited by examiner

*Primary Examiner* — James Rogers
(74) *Attorney, Agent, or Firm* — Rosenberg, Klein & Lee

(57) ABSTRACT

The present invention relates to an anti-adhesion polymer composition capable of supporting growth factor, which effectively exhibits anti-adhesion function and, at the same time, has an excellent adhesive property so as to be able to easily and continuously adhere to a wound site, has antibacterial and hemostatic properties, and is composed of an injectable formulation suitable for use in minimally invasive surgery, laparoscopic surgery or the like. The anti-adhesion polymer composition capable of supporting growth factor comprises: 24-50 wt % of a polyethyleneglycol-polypropyleneglycol-polyethyleneglycol (PEG-PPG-PEG) block copolymer having a polyethyleneglycol (PEG) content of 65-85 wt % and a molecular weight of 6,000-20,000 Da; 0.03-5 wt % of gelatin; 0.03-5 wt % of chitosan; and distilled water.

4 Claims, 1 Drawing Sheet

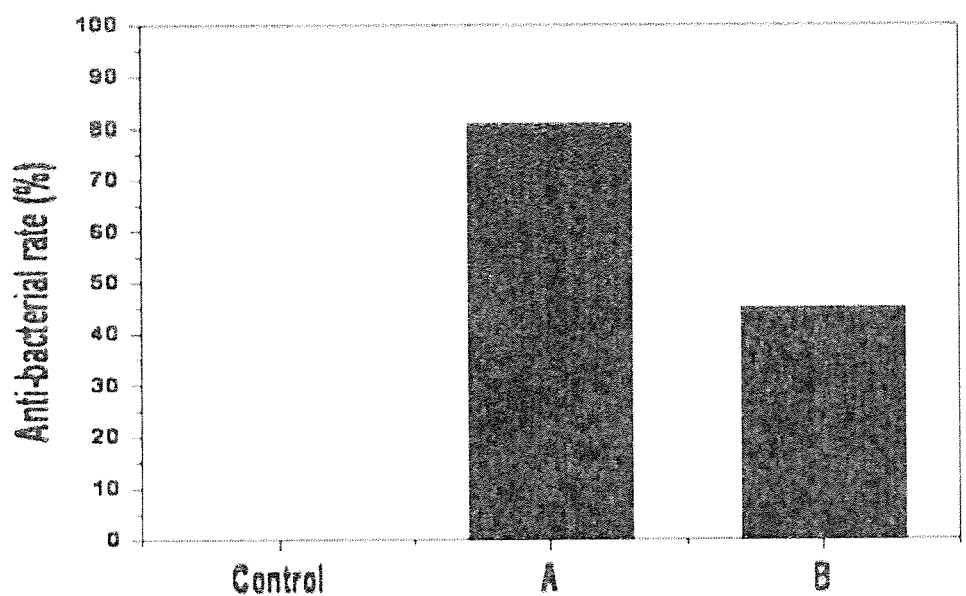

ANTI-ADHESION POLYMER COMPOSITION CAPABLE OF SUPPORTING GROWTH FACTOR

TECHNICAL FIELD

The present invention relates to an anti-adhesion polymer composition capable of supporting growth factor, and more particularly to an anti-adhesion polymer composition capable of supporting growth factor, which effectively exhibits anti-adhesive function and, at the same time, has an excellent adhesive property so as to be able to easily and continuously adhere to a wound site, has antibacterial to and hemostatic properties, and is composed of an injectable formulation suitable for use in minimally invasive surgery, laparoseopic surgery or the like. cl BACKGROUND ART As used herein, the term "adhesion" refers to a phenomenon in which blood flows out and Is coagulates during the healing of a wound caused by inflammation, friction, surgery or the like and adheres to the surrounding organ or tissue and cells penetrate into the adhered blood to produce an excessive amount of fibrous tissue. Alternatively, the term refers to a phenomenon in which blood flows out and coagulates during wound healing so that the surrounding organs or tissues, which have to be separated from each other, adhere to each other. In addition, the level of fibrin around a surgical site is increased by an inflammatory reaction occurring in the surgical site, and in this case, when fibrinolysis normally occurs, no adhesion occurs, but when fibrinolysis is inhibited by any cause, adhesion occurs.

This adhesion phenomenon causes serious problems, particularly after surgery. The adhesion phenomenon can generally occur after all kinds of surgery, and for this reason, organs or tissues around the surgical site can adhere to each other during post-surgery recovery, causing serious clinical sequelae. Generally, adhesion occurs at a frequency of about 67-93% after laparotomy, and in some cases, the adhesion is spontaneously degraded, but in most cases, the adhesion remains even after wound healing, causing various sequelae. Sequelae that are caused by adhesion after laparoscopic surgery include bowel dysfunctions, bowel obstruction, chronic pain and the like, and particularly, adhesion after obstetrical surgery is known to cause sterility (Eur. J. Surg . 1997, Supplement 577, 32-39). An anti-adhesive agent serves to prevent adhesion between issues from occurring after surgery to thereby eliminate the possibility of occurrence of secondary diseases, and thus is a very important medical product that contributes directly to the patient's safety.

In order to prevent this adhesion, the following methods have been developed and used: 1) a method of minimizing wounds during surgery; 2) a method of using an anti-inflammatory agent or activating tissue with a tissue plasminogen activator in order to prevent fibrogenesis; and 3) a method that uses an anti-adhesion barrier.

Among these methods, the use of the anti-adhesion barrier prevents adhesion between adjacent tissues from occurring during the healing of a tissue wound. This anti-adhesion barrier should prevent adhesion of a tissue wound to the adjacent tissue during the healing of the wound and should be degraded naturally or removed by absorption after a specific period of time, and either a material that is used in the anti-adhesion barrier or a degradation product thereof should be harmless to the human body.

Currently commercially available anti-adhesion agents include polyethylene glycol-polypropylene glycol (PE(-PPG), polyethylene oxide (PEO), poly(lactic acid) (PLA), hyaluronic acid, carboxymethylcellulose (CMC), fibrinogen, calcium chloride solution, dextran, an icodextrin compound, Teflon™, oxidized regenerated cellulose, polyglycan ester, poloxamer and the like.

Among such anti-adhesion agents, cellulose or dextran is a natural polymer, but is not a component derived from a living body, and thus is known to cause a foreign body reaction when it is inserted in vivo. In addition, it is known that enzymes that degrade such materials are not present in vivo and the degradation of such materials in vivo does not occur, and for this reason, such materials should be operated so that they can be oxidized or hydrolyzed. Meanwhile, an anti-adhesion solution based on hyaluronic acid is being used, but the anti-adhesion function thereof is limited, because hyaluronic acid has an in vivo half-life of only 3 days and thus is easily degraded. Among the synthetic polymers, poly(lactic acid) (PLA) has a disadvantage in that it can cause an inflammatory reaction and a foreign body reaction, because a degradation product thereof is acidic in nature.

In addition, materials used as anti-adhesion agents include a PEG-PPG-PEG block copolymer. The synthetic polymer PEG-PPG-PEG block copolymer is a polymer produced by BASE and is known as a temperature-sensitive material that is present in solution at low temperature, but is gelled at high temperature (U.S. Pat. Nos. 4,188,373, 4,478,822 and 4,474, 751). The PEG-PPG-PEG block copolymer is divided, according to the ratio of PEG to PPG, into various types. Specifically, a PEG-PPG-PEG block copolymer known as poloxamer 407 has a polyoxypropylene (PPG) molecular mass of 4,000 g/mol and a polyoxyethylene (PEG) content of 70%. Further, a polymer known as poloxamer 188 has a polyoxypropylene (PPG) molecular mass of 1,800 g/mol and a polyoxyethylene (PE( )content of 80%. The ratio between the PEG moiety and the PPG moiety, the molecular mass and acidity thereof, and additives influence the physical properties of gelatin and the polymer.

In addition, currently commercially available anti-adhesion formulations are divided into a solution type, a film type and a gel type.

First, solution-type anti-adhesion formulations have a disadvantage in that they can flow into other sites before exhibiting the anti-adhesion function or can be degraded in a too early stage, and thus do not sufficiently exhibit the anti-adhesion function in many cases.

Second, film-type anti-adhesion formulations include Seprafilm (fiyaluronic acid-CMC), Medishield (CMC-PEO), INTERCEED™ (oxidized regenerated cellulose), Surgi-Wrap (PLA) and the like, but it was reported that these products have problems in that these do not easily adhere to the surface of internal organs, or are not continuously maintained in a wound site even though they adhere to organs, and in that they are recognized as foreign matter by tissue to agglomerate to each other, and thus have an insufficient effect on the anti-adhesion of organs. In spite of such disadvantages, these formulations can surely provide an anti-adhesion barrier that is an anti-adhesion mechanism, and thus a reliable product capable of substituting for these formulations has not yet been reported. Such film-type products have been used mainly in obstetrical or spinal surgery in a limited way, and the application thereof to minimally invasive surgery, laparoscopic surgery and the like, which are current surgical trends, is greatly limited. Thus, in order to ensure anti-adhesion function, there is a need for an anti-adhesion agent that has an excellent adhesive property so as to be able to easily and continuously adhere to a wound site caused by surgery, and has an injectable formulation suitable for use in minimally invasive surgery, laparoscopic surgery and the like, which are current surgical trends.

Finally, gel-type anti-adhesion formulations are injectable formulations that have been developed in order to overcome the disadvantages of film-type and solution-type formulations. Currently commercially available gel-type anti-adhesion formulations include Hyskon™ based on dextran 70, Flowgel™ based on a PEG-PPG-PEG copolymer, ADCON based on gelatin, INTERGEL based on hyaluronic acid, and GUARDIX-sol based on hyaluronic acid-carboxymethylcellulose (CMC). The time required for wound healing varies depending on the degree of the wound, but is generally about 7 days. To ensure anti-adhesion effects, anti-adhesion formulations should assist in normal regeneration of a wound site for about 7 days, and should prevent the formation of tissue adjacent to the wound and fibrous tissue for about 7 days, after which they should be naturally degraded, absorbed and removed. However, the gel-type anti-adhesion formulations dissolve and are released before wound healing and remain in the wound tissue for an insufficient amount of time, and thus do not exhibit sufficient anti-adhesion effects. In addition, non-biomaterials such as carboxymethylcellulose and dextran have the problem of causing a foreign body reaction in vivo.

Korean Patent No. 1082935 (Nov. 7, 2011) relates to a method for preparing a porous sustained-release formulation film for preventing tissue adhesion and discloses dissolving polylactide in an organic solvent such as methyl alcohol, ethyl alcohol or acetone, preparing a porous film from the solution, and applying an antibiotic and an anti-inflammatory agent to micropores formed on the surface and inside of the film. However, polylactide, a synthetic polymer known as polylactic acid (PLA), has disadvantages in that it makes an acidic environment harmful to the human body when being degraded, because a degradation product thereof is acidic in nature, and in that it has low biocompatibility. In addition, a film prepared therefrom has a problem in that, because polylactide is dissolved in toxic organic solvents such as methyl alcohol, ethyl alcohol and acetone, these organic solvents are highly likely show toxicity in vivo when they are not completely removed during the preparation process.

Korean Patent No. 1070358 (Sep. 28, 2011) discloses a medical non-woven anti-adhesion film made of a cellulose-based short fiber that is gelled. This patent has a drawback in that, because a natural cellulose or recycled cellulose material, which is a natural polymer but is not a biomaterial, is used, it can cause a foreign body reaction when being inserted in vivo. In addition, there is a disadvantage in that, because enzymes that degrade cellulose-based materials are not present in vivo, the cellulose-based material is not completely degraded in vivo and is not released from the body in the form of degradation products.

U.S. Pat. No. 6,294,202 discloses an anti-adhesion composition in the form of water-insoluble gel, membrane, foam or fiber, which is produced by combining anionic polysaccharides such as hyaluronic acid (HA) or carboxymethyl cellulose (CMC) with a hydrophobic polymer of polyglycolide. However, carboxymethyl cellulose is not a biomaterial, and thus can cause a foreign body reaction or an inflammatory reaction in vivo. Meanwhile, polyglycolic acid (PGA) can release glycolic acid as a degradation product thereof to lower the surrounding acidity to an acidic pH that irritates the surrounding tissue to cause an inflammatory reaction. In addition, when the composition is prepared in the form of a membrane, it is hard and tends to be brittle in a dry state and rolls up upon contact with water. When the composition is prepared in the form of a membrane, foam or fiber, it is folded in vivo without being fixed or does not adhere to a portion that requires anti-adhesion, indicating that the composition is inconvenient to handle.

U.S. Pat. No. 6,280,745 B1 discloses a composition for drug delivery, which is used for the purpose of preventing adhesions. The composition comprises at least one constitutive polymer selected from the group consisting of polyoxyalkylene block copolymers, further includes a modifier polymer selected from the group consisting of cellulose ethers, sodium carboxymethylcellulose and polyacrylates, further includes a co-surfactant comprising at least one fatty acid soap and selected from among sodium oleate, sodium laurate, sodium caprate or sodium caprylate, and further includes a bioactive agent selected from various drugs including antibiotics and anti-inflammatory agents. Among the components of the composition, sodium carboxymethylcellulose (CMC-Na) is not a biomaterial, is prepared by processing cellulose obtained from plants and is known to be able to cause a foreign body reaction in vivo, and other modifier polymers including polyacrylates are not biomaterials, and thus have low biocompatibility and can cause a foreign body reaction in vivo.

Accordingly, there is still a need for an anti-adhesion agent that can effectively exhibit anti-adhesion function and, at the same time, has an excellent adhesive property so as to be able to easily and continuously adhere to a wound site occurring during surgery, and is composed of an injectable formulation suitable for use in minimally invasive surgery, laparoscopic surgery and the like, which are current surgical trends.

DISCLOSURE

Technical Problem

The present invention has been made in order to solve the above-described problems occurring in the prior art, and it is an object of the present invention to provide an anti-adhesion polymer composition which effectively exhibits anti-adhesion function and, at the same time, has an excellent adhesive property so as to be able to easily and continuously adhere to a wound site occurring during surgery, has antibacterial or hemostatic properties, and is suitable for use in minimally, invasive surgery, laparoscopic surgery and the like, which are current surgical trends.

Another object of the present invention is to an anti-adhesion polymer composition that has excellent biocompatibility so as to inhibit inflammatory reactions or foreign body reactions in vivo to the greatest possible extent.

Technical Solution

In order to accomplish the above objects, the present invention provides an anti-adhesion polymer composition capable of supporting growth factor, the composition comprising: 24-50 wt % of a polyethyleneglycol-polypropyleneglycol-polyethyleneglycol (PEG-PPG-PEG) block copolymer having a polyethyleneglycol (PEG) content of 65-85 wt % and a molecular weight of 6,000-20,000 Da; 0.03-5 wt. % of gelatin; and 0.03-5 wt % of chitosan; and distilled water.

Advantageous Effects

According to the present invention, it is possible to provide an anti-adhesion polymer composition that comprises a biopolymer such as chitosan or gelatin, and thus effectively exhibits anti-adhesion function and, at the same time, has an excellent adhesive property so as to be able to easily and continuously adhere to a wound site occurring during surgery, has antibacterial or hemostatic properties, and is composed of an injectable formulation suitable for use in minimally invasive surgery, laparoscopic surgery and the like, which are current surgical trends.

In addition, according to the present invention, it is possible to provide an anti-adhesion polymer composition that comprises a biopolymer, and thus has excellent biocompatibility so as to inhibit inflammatory reactions or foreign body reactions in vivo to the greatest possible extent,

DESCRIPTION OF DRAWINGS

FIG. 1 shows the results of evaluating the antibacterial activity of a polymer composition of the present invention in comparison with a polymer composition of the prior art.

MODE FOR INVENTION

Hereinafter, the present invention will be described in further detail,

An anti-adhesion polymer composition according to the present invention is injected in solution and applied to a wound site caused by a surgical operation, laparoscopic surgery or endoscopic surgery. The applied composition is gelled by the body temperature, thereby functioning to inhibit the adhesion of the wound site.

The PEG-PPG-PEG block copolymer that is used in the present invention may be, for example, Pluronic™ or Poloxamer™, which is commercially available from BASF (Germany). Using the temperature sensitive property of the PEG-PPG-PEG block copolymer harmless to the human body, it is possible to prepare an anti-adhesion polymer composition that is convenient to use and has an improved effect of preventing adhesion.

Particularly, the PEG-PPG-PEG block copolymer that is used in the present invention is preferably composed of two kinds of PEG-PPG-PEG block copolymers having different PEG contents, and in this case, the content of each of the block copolymers in the composition is preferably in the range of 12-25 wt %.

The content of polyoxyethylene (PEG) in the PEG-PPG-PEG block copolymer that is used in the present invention is an important factor that determines the hydrophilicity of the formulation, and thus if the content of polyoxyethylene (PEG) is too low, it will be difficult to form the formulation. For this reason, the PEG-PPG-PEG block copolymer that is used in the present invention preferably has a polyoxyethylene (PEG) content of 65-85 wt %, and more preferably 68-82 wt %.

In addition, the polymer composition of the present invention may, if necessary, further comprise about 5-25 wt % of a phase stabilizer such as glycerol in order to suppress the phase separation of the polymer composition.

Chitosan and gelatin that are added to the composition of the present invention are biopolymers and bond to the PEG-PPG-PEG block copolymer by a hydrogen bond between $O^{2-}$—$H^+$ and $N^{3-}$—$H^+$ ions and/or an ionic bond between $NH_3^{30}$—$OH^-$ functional groups. Such biopolymers serve to increase the ability of the polymer composition to adhere to a wound site so as to enhance the effect of preventing the adhesion of the wound site, thereby fixing the composition to the wound site and preventing the composition from moving to other sites.

Gelatin has a strong property of absorbing water to swell. The intestinal surface is generally known to carry a negative charge, whereas gelatin that is an intestinal surface-adhering polymer belonging to a cationic group generally carries a positive charge. Thus, electrostatic bonds between the intestinal surface and gelatin are produced to maintain the adhesion of gelatin to the intestinal surface, indicating that gelatin has excellent adhesion to the intestinal surface, that is, an excellent bioadhesive property. Furthermore, gelatin is known to increase the osmotic pressure of a wound site and promote the activation of platelets (TISSUE ENGINEERING, Volume 11, Number 78, 2005), and thus the inventive polymer composition comprising gelatin also has a hemostatic property that promotes blood coagulation.

Chitosan, a polymer belonging to a cationic group among bowel-adhering hydrogel polymers, generally carries a positive charge, and thus can form electrostatic bonds to the intestinal surface. Also, according to an electronic theory about adhesion to the bowel surface, chitosan can adhere to the bowel surface while it remains on the intestinal surface. Thus, chitosan that is used in the present invention assists in the adhesion of gelatin to the intestinal surface to enhance the adhesion of the composition to the intestinal surface. Further, chitosan is also known to exhibit an antibacterial effect due to —$NH_3$ functional groups (J. Ocul. Pharmacol. Ther. 16 (2000) 261-270) (J. Appl. Polym. Sci, 79 (2001) 1324-1335), and thus the inventive polymer composition comprising chitosan also exhibits excellent antibacterial properties.

Moreover, growth factor may be added to the anti-adhesion polymer composition of the present invention during the preparation of the composition or before application of the composition to a wound site. This anti-adhesion polymer composition forms a film by the body temperature so as to prevent le adhesion in a wound site and is gelled to release growth factor.

A method of applying the anti-adhesion polymer composition according to the present invention comprises the steps of (1) injecting the polymer composition in solution to a wound site during or after surgery; (2) fixing the polymer composition to the wound site by the biopolymer contained in the polymer composition; (3) gelling the polymer composition in solution while increasing the temperature of the composition by the body temperature; and (4) degrading and releasing the composition by in vivo enzymes and metabolism.

Due to the temperature sensitivity of the PEG-PPG-PEG block copolymer chemically bonded to have a suitable composition, the anti-adhesion polymer composition of the present invention is present in solution at room temperature by the PEG-PPG-PEG block copolymer, and when it is applied in vivo, it is gelled at a temperature of 37° C. to act as a barrier that prevents the adhesion of a wound tissue site. Because the composition is present in solution at room temperature, it can be injected into a wound site, and it is gelled after application so that it is concentrated locally at the wound site, thereby enhancing a barrier effect against adhesion.

In order for the anti-adhesion polymer composition of the present invention to exhibit preferred gelling properties at the body temperature, the composition preferably comprises 0.03-5 wt % of a biopolymer such as chitosan or gelatin and 24-50 wt. % of the PEG-PPG-PEG block copolymer.

Particularly, two kinds of PEG-PPG-PEG block copolymers having different PEG contents are preferably used after mixing them in sterile distilled water in an amount of 12-25 wt % for each copolymer and stabilizing the mixture by chemical bonds. If the content of the PEG-PPG-PEG block copolymer in the composition is too low, it will be difficult to form a gel even when the temperature increases, and if the content is too high, the composition will be gelled even at low temperature so as to be inconvenient to use. Thus, the content of the PEG-PPG-PEG block copolymer is required to controlled to a suitable level.

Meanwhile, the contents of chitosan and gelatin in the composition of the present invention are each limited to 0.03-5 wt %. If the contents of chitosan and gelatin are too low, it will be difficult to expect the effects of addition of these components, and if the content of each of these components is higher than 5 wt %, a portion of these components can remain undissolved in the polymer composition, and chitosan and gelatin in the composition can be separated when the composition is stored for a long period of time (about 3 months), suggesting that a chitosan or gelatin content of more than 5 wt % is not preferable in terms of the long-term stability of the composition.

As the molecular weight of the PEG-PPG-PEG block copolymer increases, the gelling temperature thereof increases and the miscibility thereof in the preparation of the composition decreases. Thus, the PEG-PPG-PEG block copolymer that is used in the present invention has a molecular weight of 6,000-20,000 Da, The reason is because the gelling temperature and miscibility of the PEG-PPG-PEG block copolymer are influenced by the molecular weight thereof. In view of this fact, a PEG-PPG-PEG block copolymer block copolymer having a suitable molecular weight is selected in order to optimize the formulation of the anti-adhesion polymer composition.

The anti-adhesion polymer composition of the present invention may comprise growth factor. The growth factor may be added to the composition during preparation of the composition or injected into the composition by a syringe in situ before application of the composition to a wound site, Examples of growth factor that may be used in the present invention include epidermal growth factor (EGF, beta-urogastrone), heparin-binding EGF-like growth factor (HB-EGF), transforming growth factor-α (TGF-α), fibroblast growth factors (FGFs) and the like. This growth is preferably used in an amount of 1 μg/ml to 1 mg/ml on the basis of previous animal studies in view of maintaining homeostasis and reducing side effects.

EXAMPLES

Hereinafter, the present invention will be described in detail with reference to examples. It is to be understood. however, that these examples are for illustrative purposes only and are not intended to limit the scope of the present invention.

Examples 1 to 9

3 wt % of chitosan, 15 wt % of poloxamer 188 (PEG-PPG-PEG block copolymer) and 16 wt % poloxamer 407 (PEG-PPG-PEG block copolymer) were added to sterile distilled water and were completely dissolved by stirring them using a physical stirrer at 400-500 rpm for about 2 hours in a cold process at 5~8° C. To the resulting mixture of the PEG-PPG-PEG block polymers and chitosan, 0.03-5 wt % of gelatin and 10 wt % of glycerol were added, and then the mixture was stirred for 1 hour, thereby preparing anti-adhesion polymer compositions, Comparative Example An anti-adhesion polymer composition was prepared in the same manner as described in Examples 1 to 9, except that no gelatin was added.

Measurement of Viscosity The viscosities at varying temperatures of the polymer compositions prepared in Examples 1 to 9 and the Comparative Example were measured using a Brookfield viscometer, and the results of the measurement are shown in Table 1 below.

TABLE 1

Changes in viscosity (cPs) with changes in gelatin content and temperature of polymer composition

| | Gelatin content | Viscosity (cPs) of polymer composition | | | |
|---|---|---|---|---|---|
| | | 20° C. | 25° C. | 30° C. | 35° C. |
| Example 1 | 0.03 wt % | 2280 | 2340 | 17040 | 17120 |
| Example 2 | 0.1 wt % | 2930 | 3140 | 18840 | 19300 |
| Example 3 | 0.5 wt % | 3460 | 3550 | 21300 | 21500 |
| Example 4 | 1 wt % | 3620 | 3700 | 25290 | 25640 |
| Example 5 | 1.5 wt % | 3770 | 3820 | 28330 | 28990 |
| Example 6 | 2 wt % | 3860 | 4050 | 35460 | 35760 |
| Example 7 | 3 wt % | 4150 | 5216 | 48210 | 51260 |
| Example 8 | 4 wt % | 5500 | 7840 | 56730 | 59340 |
| Example 9 | 5 wt % | 7100 | 9567 | 64940 | 67850 |
| Comparative Example | — | 1980 | 2000 | 9050 | 10203 |

As can be seen from the results in Table 1 above, as the content of gelatin increased from 0.03 wt % to 5 wt %, the viscosity at 35° C. increased by 3.96 times, suggesting that the composition has excellent adhesion to the intestines when it is applied to a wound site. The viscosity values of the composition of the Examples are about 1.7-6.6 times higher than those of the composition of the Comparative Example, indicating that the composition of the Comparative Example has low adhesion to the intestines compared to the compositions of the Examples.

Measurement of Stress

Because stress is also an index for evaluating an adhesive property, the stress of the polymer of Example 7 in Table 1 was measured and compared with those of sterile distilled water and poloxamer.

Specifically, 1 ml, of a polymer composition sample was applied and placed in an incubator at 37° C. for about 10 minutes so as to be gelled. Then, a slide glass having the sample applied thereto was fixed to a universal tester, and the polymer composition was allowed to adhere to the adaptor surface, after which the maximum stress when the polymer composition was separated from the adaptor after adhesion was measured. The results of the measurement are shown in Table 2 below.

TABLE 2

Maximum stresses of distilled water, poloxamer and the polymer composition of the present invention

| Sample | Maximum stress (MPa) |
|---|---|
| Sterile distilled water | 0.01 |
| Poloxamer control | 0.01 |
| Example 7 | 0.03 |

As can be seen from the results in Table 2 above, the stress (attractive force) of sterile distilled water or poloxamer was only 0.01 MPa, but the polymer composition of Example 7 of the present invention showed a maximum stress of 0.03 MPa, which was three times higher than that of sterile distilled water or poloxamer. This suggests that, when the polymer composition of the present invention is applied to a wound site, the flowability thereof by a fluid such as blood stream can decrease, and the composition can remain locally in the wound site, indicating that the composition has a high adhesive property.

Test for Antibacterial Activity

It is known that when an anti-adhesion polymer composition is applied during or after surgery, it is likely to be infected by antibiotic-resistance super bacteria such as Methicillin-resistant *Staphylococcus aureus* (MRSA) in the surgical field. For this reason, antibacterial activity against Methicillin-resistant *Staphylococcus aureus* (MRSA) was evaluated.

Specifically, 20 ml of each of a dilution of MRSA bacteria in TSB medium and TSB medium was mixed with 4 g of each of the polymer composition sample (A) of Example 7 of Table 1 and a commercial anti-adhesion gel product (B). Then, 100 µl of the mixture of each of the anti-adhesion polymer compositions and the bacteria was dropped onto the center of a plate medium and spread uniformly throughout the medium using a sterile spreader. Next, the bacteria were cultured at 35° C. for 24 hours, and the distribution of the bacteria was analyzed. The results of the analysis are shown in FIG. 1.

From the results shown by the graph in FIG. 1, the anti-adhesion polymer composition according to the present invention showed an antibacterial activity of about 81%, which is about 1.79 times higher than the antibacterial activity of the commercial ant-adhesion gel (45.1%). Thus, when the polymer composition of the present invention is applied to a patient during or after surgery, it can kill 81% of antibiotic-resistant super bacteria (that are likely to infect the patient in the surgical field) within 24 hours in the initial stage, and thus can reduce fatal risks such as complications caused by the infection.

Test for Hemostatic Properties

The time of blood coagulation by each of the polymer compositions prepared in the Examples of the present invention was analyzed using an activated partial thromboplastin time kit. Specifically, 0.1 mL of plasma was placed in a test tube and incubated at 37° C. for 2 minutes, and then 0.1 mL of aPPT reagent was added thereto. The mixture was incubated at 37° C. for 3 minutes. Then, 0.1 mL of the polymer composition of the present invention was added to the mixture, and the time of coagulation was measured for 10 minutes.

TABLE 3

Evaluation of hemostatic properties of the polymer compositions of the present invention

|  | Coagulation time (min) |
|---|---|
| Example 3 | 6 |
| Example 4 | 3.5 |
| Example 5 | 2.6 |
| Example 6 | 2 |
| Example 7 | 1.2 |
| Comparative Example | No coagulation |

From the results in Table 3 above, it can be seen that the inventive polymer composition containing gelatin caused blood coagulation within 6 minutes, unlike the composition of the Comparative Example, and particularly, the coagulation time did differ depending on the content of gelatin. Thus, it can be seen that the inventive polymer composition containing gelatin has a hemostatic effect.

Test for the Prevention of Adhesion by the Polymer Composition of the Present Invention The caecum surface and peritoneum of mice were artificially wounded to cause adhesions, and the wound sites were treated with the polymer compositions of Examples 5 and 7 of the present invention. After 1 week, the effects of the compositions on the prevention of adhesion of the mouse caecum and peritoneum were observed. The results are shown in Table 4 below together with the results for sterile distilled water, poloxamer and the Comparative Example for comparison. The degree of adhesion was evaluated on a six-point scale as follows: 0=no adhesion; 1=some focal adhesions: 2=many focal adhesions; 3=surface adhesion; 4=deep surface adhesion; 5=formation of blood vessels together with surface adhesion.

TABLE 4

| Sample | Mean adhesion score |
|---|---|
| Sterile distilled water | 2.5 |
| Poloxamer | 1.9 |
| Comparative Example | 1.3 |
| Example 4 | 1.0 |
| Example 7 | 0.6 |

As can be seen in Table 4 above, the degree of adhesion was about 4 times lower in the use of the polymer composition of Example 7 Mlle present invention than in the use of sterile distilled water. Also, it was 2 times lower in the use of the polymer composition of Example 7 than in the use of the composition of the Comparative Example, suggesting that the anti-adhesion property of the composition of the present invention is superior to that of the composition of the prior art.

Example 10

Measurement of Viscosity of Polymer Composition According to the Kind of PEG-PPG-PEG Block Copolymer The viscosities of polymer compositions containing sterile distilled water, 3 wt % of chitosan, 3 wt % of gelatin and varying amounts of poloxamer 188 (PEG-PPG-PEG block copolymer) and poloxamer 407 (PEG-PPG-PEG block copolymer) were measured using a Brookfield viscometer, and the results of the measurement are shown in Table 5 below.

TABLE 5

Viscosity of polymer composition according to the kind of PEG-PPG-PEG block copolymer

| Poloxamer 407:188 | 10° C. | 20° C. | 25° C. | 30° C. | 35° C. |
|---|---|---|---|---|---|
| 16:0 | 3042 | 9590 | 21780 | 43873 | 48974 |
| 16:15 | 1012 | 4150 | 5216 | 48210 | 51260 |
| 16:17 | 1278 | 5583 | 6245 | 59735 | 64146 |
| 16:20 | 2860 | 7981 | 18978 | 64754 | 65191 |

As can be seen from the results in Table 5 above, the viscosity value varied depending on the kind and composition of PEG-PPG-PEG block copolymer, and the polymer composition containing chitosan, gelatin and the PEG-PPG-PEG block copolymer consisting of poloxamer 407 alone was gelled with a rapid increase in the viscosity at 20° C., whereas the composition comprising two kinds of PEG-PPG-PEG block copolymers at a ratio of 16 wt %: 15 wt % was gelled at about 30° C. and showed a lower initial viscosity value. Thus, it can be seen that the anti-adhesion polymer composition comprising chitosan, gelatin and a single kind of PEG-PPG-PEG block copolymer is somewhat difficult to inject into a wound site, because its initial viscosity value is high, whereas the anti-adhesion polymer composition comprising two kinds of PEG-PPG-PEG block copolymers (poloxamer 407 and poloxamer 188) is more easily injected into a wound site because its initial viscosity value is low, more strongly adhere to the wound site because its final viscosity value is higher, and is easy to store and use because it has a gelling temperature of about 30° C.

INDUSTRIAL APPLICABILITY

As described above, the anti-adhesion polymer composition of the present invention effectively exhibits anti-adhesion function and, at the same time, has an excellent adhesive property so as to be able to easily and continuously adhere to a wound site, has antibacterial and hemostatic properties, and can be effectively used to prevent the adhesion of a wound site during or after minimally invasive surgery or laparoscopic surgery.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An anti-adhesion polymer composition consisting essentially of: 24-50wt % of a polyethyleneglycol-polypropyleneglycol-polyethyleneglycol (PEG-PPG-PEG) block copolymer having a polyethyleneglycol (PEG) content of 65-85wt % and a molecular weight of 6,000-20,000Da; 0.03-5wt % of gelatin; 0.03-5wt % of chitosan; distilled water; glycerol as a stabilizer for suppressing phase separation of the composition; and at least one growth factor selected from the group consisting of epidermal growth factor (EGF, beta-urogastrone), heparin-binding EGF-like growth factor (HB-EGF), transforming growth factor-$\alpha$ (TGF-$\alpha$) and fibroblast growth factors (FGFs).

2. The anti-adhesion polymer composition of claim 1, wherein the block copolymer is composed of two kinds of block copolymers having different weight % of PEG.

3. The anti-adhesion polymer composition of claim 2, wherein the amount of each of the block copolymers in the composition is 12-25wt %.

4. The anti-adhesion polymer composition of claim 1, wherein said composition forms an injectable solution which is capable of adhering to a wound site.

* * * * *